(12) United States Patent
Sakurada

(10) Patent No.: US 11,707,069 B2
(45) Date of Patent: Jul. 25, 2023

(54) AGENTS HAVING EFFICACY AGAINST VIRUSES, ALLERGENS, BACTERIA AND ODORANTS, MATERIALS INCLUDING SAID AGENTS, AND METHODS FOR PRODUCING SAID AGENTS

(71) Applicant: SHINSHU CERAMICS CO., LTD., Nagano (JP)

(72) Inventor: Tsukasa Sakurada, Nagano (JP)

(73) Assignee: SHINSHU CERAMICS CO., LTD., Nagano (JP)

( * ) Notice: Subject to any disclaimer, the term of this patent is extended or adjusted under 35 U.S.C. 154(b) by 0 days.

(21) Appl. No.: 17/015,016

(22) Filed: Sep. 8, 2020

(65) Prior Publication Data

US 2021/0068399 A1   Mar. 11, 2021

(30) Foreign Application Priority Data

Sep. 9, 2019 (JP) ................. 2019-164063

(51) Int. Cl.
| | |
|---|---|
| A01N 59/20 | (2006.01) |
| A61K 33/242 | (2019.01) |
| A61K 33/38 | (2006.01) |
| A61K 33/243 | (2019.01) |
| A61K 33/34 | (2006.01) |
| A61K 33/42 | (2006.01) |
| C09D 5/14 | (2006.01) |
| D06M 11/83 | (2006.01) |
| D06M 11/70 | (2006.01) |

(52) U.S. Cl.
CPC ............ *A01N 59/20* (2013.01); *A61K 33/242* (2019.01); *A61K 33/243* (2019.01); *A61K 33/34* (2013.01); *A61K 33/38* (2013.01); *A61K 33/42* (2013.01); *C09D 5/14* (2013.01); *D06M 11/70* (2013.01); *D06M 11/83* (2013.01)

(58) Field of Classification Search
None
See application file for complete search history.

(56) References Cited

U.S. PATENT DOCUMENTS

| | | | | |
|---|---|---|---|---|
| 9,144,237 | B2 * | 9/2015 | Sakurada ................ | A61P 17/02 |
| 10,051,859 | B2 * | 8/2018 | Sakurada ................ | A61P 31/10 |
| 11,033,026 | B2 * | 6/2021 | Sakurada ................ | A61P 17/00 |
| 2014/0044801 | A1 * | 2/2014 | Sakurada ................ | A61P 17/04 |
| | | | | 156/308.2 |

FOREIGN PATENT DOCUMENTS

| | | |
|---|---|---|
| JP | 5995100 B2 | 9/2016 |
| JP | 2016199560 A | 12/2016 |

* cited by examiner

*Primary Examiner* — Dominic Lazaro
(74) *Attorney, Agent, or Firm* — Hauptman Ham, LLP

(57) ABSTRACT

The present invention provides agents having efficacy against viruses, allergens, bacteria and odorants, materials including such agents, and methods for producing the agents. An agent according to an embodiment of the present invention includes titanium dioxide particles having low photocatalytic activity, and metal ions of at least one metal selected from gold, silver, platinum and copper that are adsorbed to the surface of the titanium dioxide particles. The agent may further include hydroxyapatite particles, and the metal ions may be adsorbed also to the surface of the hydroxyapatite. The metal ions may be at least partially present in the form of at least one of an oxide of the metal, a hydroxide of the metal, and the elemental metal.

23 Claims, 4 Drawing Sheets

AGENTS HAVING EFFICACY AGAINST VIRUSES, ALLERGENS, BACTERIA AND ODORANTS, MATERIALS INCLUDING SAID AGENTS, AND METHODS FOR PRODUCING SAID AGENTS

RELATED APPLICATIONS

The present application claims priority to Japanese Patent Application No. 2019-164063, filed Sep. 9, 2019, the disclosure of which is hereby incorporated by reference herein in its entirety.

BACKGROUND OF THE INVENTION

1. Field of the Invention

The present invention relates to agents having efficacy against viruses, allergens, bacteria and odorants, to materials including such agents, and to methods for producing the agents.

2. Description of the Related Art

Sterilizing agents and deodorizing agents in the form of solid or liquid are conventionally known. Most solid sterilizing agents and deodorizing agents are products of the photocatalyst-related technology utilizing the oxidation-reduction ability of photocatalysts. While photocatalysts are usually insoluble themselves and thus can function over long periods of time, they are active only in the presence of UV light and are inactive in the dark. In addition, photocatalysts, because of their being solid, produce sterilizing effects and deodorizing effects only when bacteria, viruses, allergens and various odor causing organic matters are brought into contact therewith, and thus take time to effectively kill bacteria or remove the odor in the surrounding environment. In contrast, liquid sterilizing agents or deodorizing agents such as alcohols and hypochlorites can usually function without light to effectively kill bacteria or eliminate the odor in the surrounding environment immediately, but they vaporize or evaporate quickly to function only for short periods of time. Furthermore, many of the liquid sterilizing agents are generally toxic and therefore have the disadvantage of burdening the environment.

For example, conventional photocatalysts are composed of photocatalytic titanium dioxide as a carrier, and metallic silver supported on the carrier, and offer sterilizing effects and deodorizing effects by decomposing bacteria, viruses, allergens and various odor causing organic matters by the action of radicals stemming from the oxidation-reduction reaction occurring on the surface of the photocatalysts in the presence of UV light. However, this oxidation-reduction reaction occurs only at the interface of photocatalytic silver and titanium dioxide, and the reaction is very weak under visible light. Thus, the photocatalysts are not useful in dark environments.

To solve the problems of these conventional photocatalysts, for example, Japanese Patent No. 5995100 and Japanese Unexamined Patent Publication No. 2016-199560 disclose agents capable of persistent sterilizing effects or deodorizing effects over long periods of time even in the absence of light irradiation. These agents include metal particles and ceramic particles including titanium dioxide. The metal particles and the ceramic particles are bonded together partially in such a manner that one of the particles is ingrown into the other particles to form metal-ceramic joint particles. The metal particles are selected from gold, silver, platinum, copper and combinations thereof.

At the SAT Technology Showcase held on Jan. 29, 2019, at International Congress Center EPOCHAL TSUKUBA, Japan, Qi Zhu (National Institute of Advanced Industrial Science and Technology), et al. reported a study in which titanium dioxide impregnated with a nitric acid solution of a silver salt was placed into a high-pressure reaction vessel, and was heated and washed with ethanol to give a silver ion-bearing titanium dioxide catalyst (Poster No. P-60 (Study of catalytic antibacterial activity of titanium dioxide modified with silver ions)). According to the study, this silver ion-bearing titanium dioxide catalyst exhibited a bactericidal activity against *Escherichia coli* even under dark conditions in water, but released about 0.09 mg/L silver ions in 24 hours.

The conventional titanium dioxide catalysts bearing silver ions are designed to exhibit a sterilizing function even under low illuminance while ensuring that the photocatalytic properties of titanium dioxide are not impaired. Unfortunately, these conventional titanium dioxide catalysts have a problem in that substrates and organic materials supporting the catalysts are decomposed when placed under light.

The present invention has been made to solve the problems in the art discussed above. That is, an object of the present invention is to provide agents that are capable of photocatalyzing oxidation-reduction reaction with an optimum intensity even in the presence of light and can exhibit efficacy against viruses, allergens, bacteria and odorants over long periods of time. Other objects of the present invention are to provide materials including such agents, and to provide methods for producing the agents.

SUMMARY OF THE INVENTION

In one aspect of the present invention, an agent having efficacy against at least one of viruses, allergens, bacteria, fungi and odorants includes titanium dioxide particles having low photocatalytic activity, and metal ions of at least one metal selected from gold, silver, platinum and copper that are adsorbed to the surface of the titanium dioxide particles.

Titanium dioxide is white and has high light-shielding properties, and thus has found wide use as pigments. Titanium dioxide used as pigments in products such as paints and cosmetics is of low photocatalytic activity to prevent the decomposition of surrounding organic substances. Furthermore, some of such titanium dioxide pigments are coated with inorganic materials on the surface to further depress the photocatalytic activity.

Similarly to titanium dioxide used as, for example, pigments, the titanium dioxide particles used in the present invention are of lower photocatalytic activity than usual titanium dioxide used as photocatalysts. Most commercial titanium dioxide particles have lower photocatalytic activity than usual titanium dioxide photocatalysts. Thus, commercial inexpensive titanium dioxide particles may be used as such in the agent according to the present invention, offering economic advantages.

The agent according to the currently discussed aspect of the present invention includes such titanium dioxide particles having low photocatalytic activity, and metal ions of at least one selected from gold, silver, platinum and copper that are adsorbed on the surface of the titanium dioxide particles having low photocatalytic activity. The metal ions of at least one selected from gold, silver, platinum and copper are known to have, depending on their types, various levels of antiviral effects, antiallergenic effects, sterilizing effects, antifungal effects or anti-odorant effects regardless of the presence or absence of light. In addition, the titanium dioxide particles used in the agent according to the present invention are photocatalytically active, although to a very limited extent, and thus can favorably decompose dead organisms such as of viruses, bacteria and fungi, allergens, odor substances and further soiling substances, in combination with the metal ions of at least one selected from gold, silver, platinum and copper that are attached to the surface of the titanium dioxide particles. Thus, the agent according to the currently discussed aspect of the present invention exhibits a high level of efficacy against at least one of viruses, allergens, bacteria, fungi and odorants over long periods of time regardless of the presence or absence of light. For example, the agent according to the currently discussed aspect of the present invention does not substantially release silver ions into water (the amount of silver ion release is as small as several ppb). Thus, the agent according to the currently discussed aspect of the present invention decomposes dead organisms such as of viruses, bacteria and fungi, allergens, odor substances and soiling substances, mainly by way of contact therewith. Furthermore, the agent according to the currently discussed aspect of the present invention is substantially free from silver ion release and thus exhibits efficacy against at least one of viruses, allergens, bacteria, fungi, odorants, harmful substances and the like over long periods of time.

In addition, the agent according to the currently discussed aspect of the present invention contains titanium dioxide particles that are less photocatalytically active than usual photoactive titanium dioxide, and thus allows a substrate or an organic material bearing the agent to last for an appropriate amount of lifetime even under illuminated conditions while ensuring efficacy against at least one of viruses, allergens, bacteria, fungi, odorants, harmful substances and the like.

The agent according to the currently discussed aspect preferably further includes hydroxyapatite (HAp) particles, and the metal ions are preferably adsorbed also to the surface of the hydroxyapatite.

Hydroxyapatite is a component that is known to favorably adsorb viruses, allergenic substances, bacteria, fungi, odorants, harmful substances and the like. In the currently discussed aspect of the present invention, the hydroxyapatite is surrounded by the agent that has efficacy against at least one of viruses, allergens, bacteria, fungi, odorants, harmful substances and the like. Thus, the agent exhibits a high level of efficacy against at least one of viruses, allergens, bacteria, fungi, odorants, harmful substances and the like by favorably destroying or decomposing viruses, allergenic substances, bacteria, fungi, odorants, harmful substances and the like adsorbed to the hydroxyapatite.

In the agent according to the currently discussed aspect, the metal ions may be at least partially present in the form of at least one of an oxide of the metal, a hydroxide of the metal, and the elemental metal.

When metal ions of at least one selected from gold, silver, platinum and copper are adsorbed to the surface of titanium dioxide particles in a solution, and the particles are thereafter dried, part of the metal ions that have been adsorbed naturally converts to the hydroxide (the hydrate of the oxide) and then to the oxide with the progress of dehydration, and is further partially photodecomposed particularly by the surrounding light into the corresponding metal element. Thus, as long as the agent is not absolutely dry, the agent in the currently discussed aspect contains the metal not only in the form of metal ions naturally adsorbed to the surface of the titanium dioxide particles due to the surrounding humidity, but also in the form of oxide and hydroxide of the metal as well as the elemental metal. Thus, the agent can remain effective against at least one of viruses, allergens, bacteria, fungi and odorants regardless of the presence or absence of light.

In another aspect of the present invention, an agent having efficacy against at least one of viruses, allergens, bacteria, fungi and odorants includes titanium dioxide particles having low photocatalytic activity, and metal ions of at least one metal selected from gold, silver, platinum and copper that are adsorbed to the surface of the titanium dioxide particles.

The agent according to the present aspect of the present invention includes metal ions of at least one selected from gold, silver, platinum and copper on the surface of titanium dioxide particles having low photocatalytic activity, and thus exhibits a high level of efficacy against at least one of viruses, allergens, bacteria, fungi and odorants over long periods of time regardless of the presence or absence of light. In addition, the agent in the currently discussed aspect is inexpensive because, in particular, it does not contain metal particles of at least one selected from gold, silver, platinum and copper. For example, the agent according to the currently discussed aspect of the present invention does not substantially release silver ions into water (the amount of silver ion release is as small as several ppb). Thus, the agent according to the currently discussed aspect of the present invention decomposes dead organisms such as of viruses, bacteria and fungi, allergens, odor substances and soiling substances, mainly by way of contact therewith. Furthermore, the agent according to the present aspect of the present invention is substantially free from silver ion release and thus exhibits efficacy against at least one of viruses, allergens, bacteria, fungi, odorants, harmful substances and the like over long periods of time.

The agent according to the currently discussed aspect of the present invention may further include hydroxyapatite particles, and the metal ions may be adsorbed also to the surface of the hydroxyapatite.

By utilizing the high capability of the hydroxyapatite particles of adsorbing viruses, allergenic substances, bacteria, fungi and odorants, the agent according to the currently discussed aspect can exhibit a high level of efficacy against at least one of viruses, allergens, bacteria, fungi, odorants, harmful substances and the like regardless of the presence or absence of light.

In the agent according to the currently discussed aspect, the metal ions may be at least partially present in the form of at least one of an oxide of the metal, and a hydroxide of the metal.

When metal ions of at least one selected from gold, silver, platinum and copper are adsorbed to the surface of titanium dioxide particles in a solution, and the particles are thereafter dried, part of the metal ions that have been adsorbed naturally converts to the hydroxide (the hydrate of the oxide) and then to the oxide with the progress of dehydration, and is further partially photodecomposed particularly by the surrounding light into the corresponding metal element. Thus, as long as the agent is not absolutely dry, the agent in the currently discussed aspect contains the metal not only in the form of metal ions naturally adsorbed to the surface of the titanium dioxide particles due to the surrounding humidity, but also in the form of oxide and hydroxide of the metal as well as the elemental metal. Thus, the agent can maintain a high level of efficacy against at least one of viruses, allergens, bacteria, fungi, odorants, harmful substances and the like regardless of the presence or absence of light.

Furthermore, a material in an aspect of the present invention includes the agent according to any of the aspects described above.

The material according to the currently discussed aspect exhibits a high level of efficacy against at least one of viruses, allergens, bacteria, fungi, odorants, harmful substances and the like over long periods of time regardless of the presence or absence of light.

The material according to the currently discussed aspect may be applied to at least one substrate selected from:

(a) at least one of fibers of any of woven fabrics, nonwoven fabrics and paper, wood, plastics, metals and ceramics, (b) compound materials formed of two or more of woven fabrics, nonwoven fabrics, paper, wood, plastics, metals and ceramics, and (c) at least one of paints, resin films, water, cleaning solutions, air filters and printing inks.

The material according to the currently discussed aspect may be applied to a substrate such as fibers of a woven fabric, a nonwoven fabric or paper, wood, a plastic, a metal or a ceramic bearing the agent according to one aspect of the present invention to allow the substrate to exhibit a high level of efficacy against at least one of viruses, allergens, bacteria, fungi and odorants over long periods of time regardless of the presence or absence of light while ensuring that the substrate has an appropriately long lifetime. Furthermore, the material may be applied to other substrates such as paints, resin films, water, cleaning solutions, air filters and printing inks.

The material in the currently discussed aspect may be such that the substrate is fibers of any of a woven fabric, a nonwoven fabric and paper, and the fibers are impregnated with the agent by immersion of the fibers into a solution in which the agent is dispersed in a solvent, or the agent is attached to the surface of the fibers by application, to the surface of the fibers, of a solution in which the agent is dispersed in a solvent. Furthermore, the fibers may be in the form of any of a fibrous sheet, a fibrous pillow case, a towel, a gauze, a curtain, a garment, a gown and an adhesive plaster (an adhesive bandage).

The material according to the currently discussed aspect allows for the obtaining of fibers, fibrous sheets, fibrous pillow cases, towels, gauzes, curtains, garments, gowns and adhesive plasters (adhesive bandages) that each exhibit a high level of efficacy against at least one of viruses, allergens, bacteria, fungi, odorants, harmful substances and the like regardless of the presence or absence of light. To enhance the bond strength of the agent with respect to the fibers, a known binder may be used in the dispersion solution of the agent in a solvent, and the agent together with the binder may be attached to the surface of the fibers.

The material according to the currently discussed aspect may be such that the substrate is at least one of wallpapers, ceiling materials, flooring materials and furniture, and a solution in which the agent is dispersed in a solvent is applied to the surface of the substrate, or a resin film including the agent is applied to the surface of the substrate.

The material according to the currently discussed aspect allows for the obtaining of wallpapers, ceiling materials, flooring materials and furniture that each exhibit, on the surface thereof, a high level of efficacy against at least one of viruses, allergens, bacteria, fungi, odorants, harmful substances and the like regardless of the presence or absence of light. In this case too, the bond strength of the agent with respect to the surface of wallpapers, ceiling materials, flooring materials and furniture may be enhanced by using a known binder in the dispersion solution of the agent in a solvent, and attaching the agent to the surface of wallpapers, ceiling materials, flooring materials and furniture together with the binder. When a resin film is applied to the surface of the substrate, an appropriate adhesive or pressure-sensitive adhesive may be used.

Furthermore, the material according to the currently discussed aspect may be applied to any of drinking water, rainwater, hot spring and cooling towers. Furthermore, the material according to the currently discussed aspect may be applied to any of hydroponic culture (including aquaculture), soil amendment, washing and cleaning of vegetables, foodstuff preservation and foodstuff antisepsis.

The material according to the currently discussed aspect allows for the obtaining of drinking water, rainwater, hot spring, cooling towers, hydroponic culture (including aquaculture), soil amendment, washing and cleaning of vegetables, foodstuff preservation and foodstuff antisepsis that each exhibit or benefit from, on the surface thereof, a high level of efficacy against at least one of viruses, allergens, bacteria, fungi, odorants, harmful substances and the like regardless of the presence or absence of light.

A product according to an aspect of the present invention includes any of the agents described hereinabove.

The product according to the currently discussed aspect exhibits, on the surface thereof, a high level of efficacy against at least one of viruses, allergens, bacteria, fungi, odorants, harmful substances and the like regardless of the presence or absence of light.

The products according to the currently discussed aspect are of great variety, such as those selected from:

(1) fibrous sheets, bed sheets, pillow cases, towels, handkerchiefs, bed-bath cloths, curtains, futon covers, blanket covers, seat covers, floor cushion covers, covers, table clothes, carpets, air-purification filters, water-purification filters, air conditioners and vehicles, (2) medical items selected from medical materials, medical elements, medical products and medical equipment, (3) adhesive plasters (adhesive bandages), ointments, skin lotions, cosmetics, hand creams, gauzes, catheters, endoscopes, bandages, gowns, face masks, balloons, medical instrument buttons, and resin products for medical use, (4) medical agents applied to at least one of tinea pedis, burn (scald), bedsore (decubitus), secondary diseases of atopic dermatitis, and wounds in skin or epidermis, and (5) infection control.

A wide variety of the products according to the currently discussed aspect exhibit, on the surface thereof, a high level of efficacy against at least one of viruses, allergens, bacteria, fungi, odorants, harmful substances and the like regardless of the presence or absence of light.

One aspect of the present invention resides in a method for producing an agent having efficacy against at least one of viruses, allergens, bacteria, fungi, odorants, harmful substances and the like, including:

a first step of providing a solution including metal ions of at least one metal selected from gold, silver, platinum and copper, a second step of immersing titanium dioxide particles having low photocatalytic activity into the solution and thereby adsorbing the metal ions to the surface of the titanium dioxide, and a third step of drying the particles obtained at the second step.

In the agent production method according to the currently discussed aspect, hydroxyapatite particles may be present at the second step.

In the agent production method according to the currently discussed aspect, the metal ions of at least one metal provided at the first step may be formed by the electrolysis of the at least one metal, or by the addition of a salt of the at least one metal, and the second step may be performed by manual stirring, mechanical stirring, ultrasonication, inert gas bubbling or ball mill stirring.

The agent production method according to any of the above-described aspect can easily produce the agents according to the present invention described hereinabove. In the agent production method according to the currently discussed aspect, the solution provided at the first step that includes metal ions of at least one selected from gold, silver, platinum and copper may be formed by performing electrolysis in the solution using an electrode made of the metal, or by dissolving a salt of the metal.

In the agent production method according to any of the above-described aspect, the second step may be performed by simply allowing the mixture to stand still. However, manual stirring, mechanical stirring, ultrasonication, inert gas bubbling or ball mill stirring allows the metal ions of at least one selected from gold, silver, platinum and copper to be adsorbed to the titanium dioxide particles in a smaller amount of time.

Newly Added:

In the agent production method according to any of the above-described aspect, the third step may include, concurrently with drying, bonding or attaching the metal ions of at least one metal selected from gold, silver, platinum and copper, and the titanium dioxide particles to a substrate such as fibers with a resin or the like. In this manner, efficacy against at least one of viruses, allergens, bacteria, fungi, odorants, harmful substances and the like may be easily imparted to the substrate.

DETAILED DESCRIPTION OF EMBODIMENTS

The following illustrates in detail agents according to the present invention having efficacy against at least one of viruses, allergens, bacteria, fungi and odorants, materials including the agents, and methods for producing the agents, based on Examples and Comparative Example. However, it should be construed that Examples described hereinbelow only give some exemplary concrete forms to the technical idea of the present invention, and do not intend to limit the scope of the present invention to such Examples. The present invention may be equally applied to other embodiments that fall within the scope of the claims.

Preparation of Textile Sample of Example 1

In Example 1, commercial white pigment KRONOS titanium dioxide KA-10C (product name, Titan Kogyo, Ltd.) was used as base titanium dioxide particles. According to the catalogue, these titanium dioxide particles are of anatase type but are low in photocatalytic activity, and will not cause significant photodecomposition when added to a paint. Furthermore, commercial high-purity calcium phosphate ($3Ca(PO_4)_2 \cdot Ca(OH)_2$) (Toko Techno) was used directly as hydroxyapatite (HAp) particles.

Figure 1B:
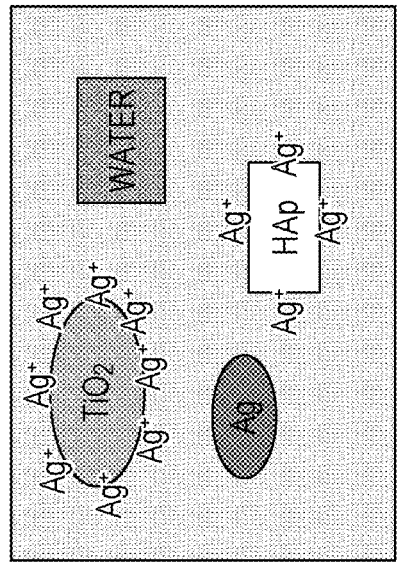
FIGS. 1A to 1D are views illustrating steps for forming an agent of Example 1 on the surface of a textile as a substrate.
Figure 1D:
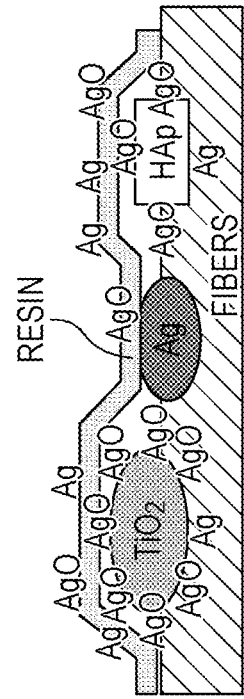
Figure 1A:
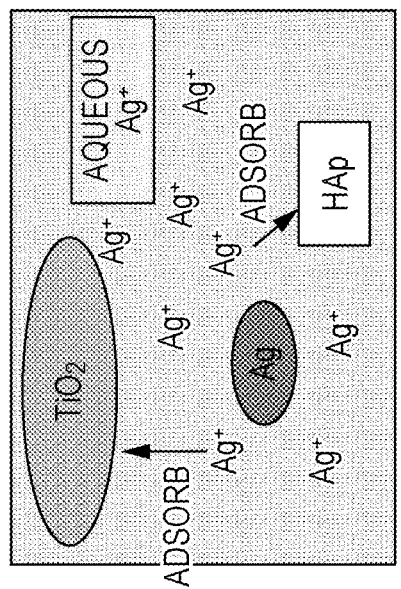

Equal amounts of the titanium dioxide particles and the hydroxyapatite particles were dispersed in distilled water, and an appropriate amount of silver metal particles were also dispersed in the distilled water. Next, electrolysis was performed for a short time using a silver metal plate as the anode and a platinum metal plate as the cathode, thereby forming silver ions in the distilled water. Incidentally, the silver metal particles may be added at a small dose, and preferably have a small grain size to ensure that the equilibrium reaction of silver and silver ions will proceed quickly. The average particle size of the silver metal particles may be about 100 nm to 1 μm, although not limited thereto. The state of the system at this stage is schematically illustrated in FIG. 1A. The system was allowed to stand still overnight to allow silver ions to sufficiently adsorb to the surface of the titanium dioxide particles and the hydroxyapatite particles. The state of the system at this stage is schematically illustrated in FIG. 1B. In the manner described above, silver ions were adsorbed to the titanium dioxide and to the hydroxyapatite in water. The system at this stage is an aqueous dispersion of the titanium dioxide bearing silver ions, the hydroxyapatite bearing silver ions, and the silver metal particles.

Figure 1C:
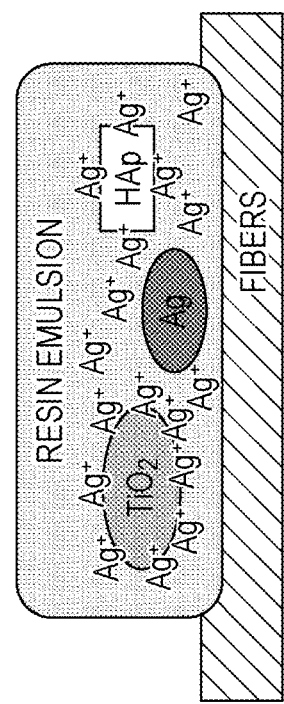

Next, the titanium dioxide bearing silver ions, the hydroxyapatite bearing silver ions, and the silver metal particles were collected by filtration and were dispersed in an aqueous solution of an acrylic resin as a binder, thus forming an emulsion of the titanium dioxide bearing silver ions, the hydroxyapatite bearing silver ions, and the silver metal particles. Thereafter, a sterilized gauze was immersed into the emulsion to attach the titanium dioxide bearing silver ions, the hydroxyapatite bearing silver ions, and the silver metal particles to the gauze. The wet gauze at this stage is schematically illustrated in FIG. 1C.

Furthermore, the wet gauze was sufficiently dried in a desiccator. A textile sample of Example 1 was thus obtained. During drying, part of the silver ions that have been adsorbed to the titanium dioxide and the hydroxyapatite react with water and convert to silver hydroxide (AgOH or $Ag_2O \cdot H_2O$) and then to silver oxide ($Ag_2O$), and the silver hydroxide or the silver oxide is further partially photodecomposed by external light into silver atoms. That is, in the dry state, the silver ions adsorbed to the titanium dioxide and the hydroxyapatite come to exist partially as silver hydroxide and silver oxide and further partially as elemental silver metal that, adds, although not identifiable, to the silver metal originally present there. The state of the product at this stage is schematically illustrated in FIG. 1D. In FIG. 1D, silver oxide and silver hydroxide are collectively indicated simply as "AgO" to help understanding.

Preparation of Textile Sample of Example 2

Figure 2B:
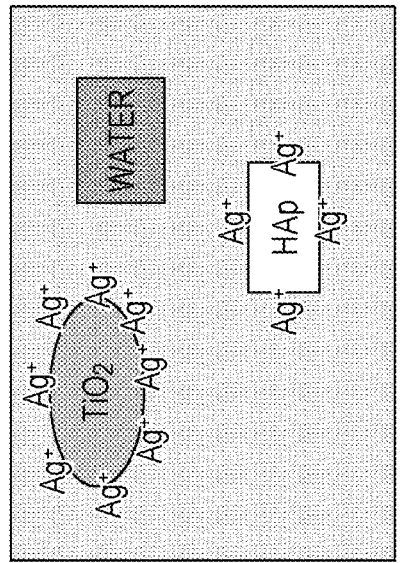
FIGS. 2A to 2D are views illustrating steps for forming an agent of Example 2 on the surface of a textile as a substrate.
Figure 2D:
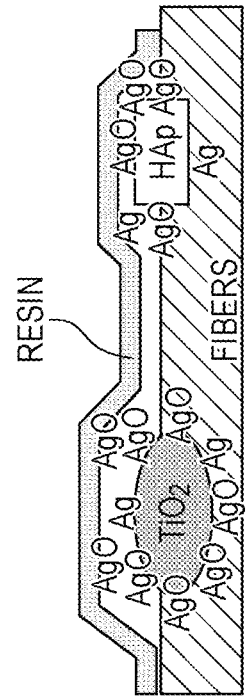
Figure 2A:
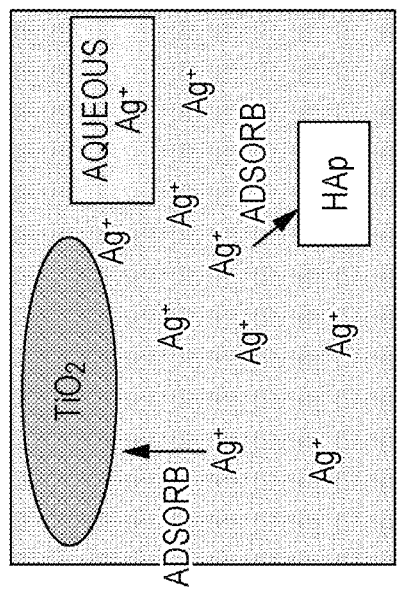

The production of a textile sample of Example 2 will be described with reference to FIGS. 2A to 2D. The base titanium dioxide particles and the hydroxyapatite (HAp) particles used in Example 2 were the same as the materials used in Example 1. Equal amounts of the titanium dioxide particles and the hydroxyapatite particles were dispersed in distilled water. Unlike in Example 1, no silver metal was dispersed in the distilled water in Example 2. Next, electrolysis was performed for a short time using a silver metal plate as the anode and a platinum metal plate as the cathode, thereby forming silver ions in the distilled water. The state of the system at this stage is schematically illustrated in FIG. 2A. The system was allowed to stand still overnight to allow silver ions to sufficiently adsorb to the surface of the titanium dioxide particles and the hydroxyapatite particles. The state of the system at this stage is schematically illustrated in FIG. 2B. The system at this stage is an aqueous dispersion of the titanium dioxide bearing silver ions, and the hydroxyapatite bearing silver ions.

Figure 2C:
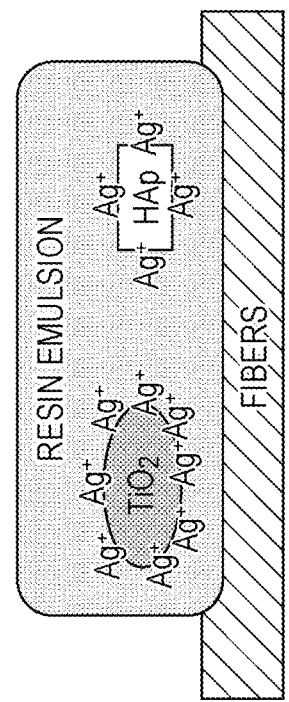

Next, the titanium dioxide bearing silver ions, and the hydroxyapatite bearing silver ions were collected by filtration and were dispersed in an aqueous solution of an acrylic resin as a binder, thus forming an emulsion of the titanium dioxide bearing silver ions, and the hydroxyapatite bearing silver ions. Thereafter, a sterilized gauze was immersed into the emulsion to attach the titanium dioxide bearing silver ions, and the hydroxyapatite bearing silver ions to the gauze. The wet gauze at this stage is schematically illustrated in FIG. 2C.

Furthermore, the wet gauze was sufficiently dried in a desiccator. A textile sample of Example 2 was thus obtained. During drying, part of the silver ions that have been adsorbed to the titanium dioxide and the hydroxyapatite react with water and convert to silver hydroxide (AgOH or $Ag_2O \cdot H_2O$) and then to silver oxide ($Ag_2O$), and the silver hydroxide or the silver oxide is further partially photodecomposed by external light into silver atoms. That is, in the dry state, the silver ions adsorbed to the titanium dioxide and the hydroxyapatite come to exist partially as silver hydroxide and silver oxide and further partially as elemental silver metal that is, however, not identifiable. The state of the product at this stage is schematically illustrated in FIG. 2D. In FIG. 2D, to help understanding, silver oxide and silver hydroxide are collectively indicated simply as "AgO", and the individual silver atoms are not illustrated.

Preparation of Textile Sample of Comparative Example 1

A textile sample of Comparative Example 1 was prepared in the same manner as in Example 2, except that the titanium dioxide pigment used as the base material in Example 2 was replaced by commercial high-purity alumina particles AKP-20 (product name, Sumitomo Chemical Co., Ltd.). The textile sample of Comparative Example 1 has the same configuration as that of the textile sample of Example 2 illustrated in FIG. 2D, except that titanium dioxide as the base material is replaced by aluminum oxide ($Al_2O_3$).

Antibacterial Activity Evaluation 1 and Procedures

The textile sample of Example 1 and the textile sample of Example 2, although differing in the size of the silver metal particles, have substantially the same configurations. Thus, the textile sample of Example 2 and the textile sample of Comparative Example 1 were tested by the absorption method in accordance with JIS L 1902 to evaluate their antibacterial activity as described below. The antibacterial activity test includes the following steps (1) to (4).

(1) A 5 cm×5 cm sheet (approximately 0.4 g) cut from the textile sample of Example 2 or Comparative Example 1 is placed into a 50 mL centrifuge tube.

(2) A $10^6$ CFU/mL solution of bacteria (in saline) is provided and is diluted with a 20-fold diluted culture solution in accordance with JIS L 1902 to give a $10^5$ CFU/mL bacterial solution.

(3) A 0.1 mL portion (corresponding to $10^4$ CFU/0.1 mL) of the $10^5$ CFU/mL bacterial solution is inoculated to the textile sample in the centrifuge tube. During this process, all the bacterial solution is allowed to penetrate into the textile sample sufficiently without any residual bacterial solution.

(4) The centrifuge tube is closed with the lid and is stored in an incubator kept at 35° C. The bacteria are washed out 18 hours later, and the bacterial counts are measured.

Three types of bacteria were used:
(i) *Staphylococcus aureus*,
(ii) *Klebsiella pneumoniae*, and
(iii) *Escherichia coli*. Three sheets of the textile sample of Example 2 and three sheets of the textile sample of Comparative Example 1 were repeatedly washed 50 times (50 times of washing), and other triplets of the textile samples were repeatedly washed 100 times (100 times of washing). With respect to these washed sheets, the antibacterial activity was evaluated by measuring the bacterial counts immediately after the inoculation (0 hr) and after incubation (18 hr), the results being averaged. The results are described in Table 1.

The lower values in the "0 hr" column and the "18 hr" column in Table 1 are the viable bacterial counts, and the upper values are the common logarithms thereof. The antibacterial activities (the growth values) are values determined from the following equation:

Antibacterial activity (growth value)=(log $B$-log $A$)-(log $D$-log $C$)

A: Viable bacterial count on standard textile immediately after inoculation
B: Viable bacterial count on standard textile after incubation
C: Viable bacterial count on sample immediately after inoculation
D: Viable bacterial count on sample after incubation

TABLE 1

| | | *Staphylococcus aureus* (N = 3) | | | | *Klebsiella pneumoniae* (N = 3) | | | |
|---|---|---|---|---|---|---|---|---|---|
| | | 0 hr | 18 hr | Antibacterial activity (growth value) | Reduction rate (%) | 0 hr | 18 hr | Antibacterial activity (growth value) | Reduction rate (%) |
| Autoclaved controls (standard textiles) | | 4.9 118,000 | 7.4 48,000,000 | 2.5 | 0 | 4.9 74,000 | 8.0 106,000,000 | 3.0 | 0 |
| Example 2 | 50 Times of washing | 5.0 98,000 | 3.6 3,623 | 4.1 | 99.99 | 4.8 66,000 | 1.3 20 | 6.7 | 99.99 |
| | 100 Times of washing | 5.0 112,000 | 3.3 1,793 | 4.4 | 99.99 | 4.9 74,000 | 1.3 20 | 6.7 | 99.99 |
| Comparative Example 1 | 50 Times of washing | 4.9 88,000 | 5.7 473,333 | 1.7 | 97.94 | 4.8 66,000 | 6.2 1,593,940 | 1.8 | 98.49 |
| | 100 Times of washing | 5.1 118,000 | 6.7 4,840,000 | 0.9 | 78.95 | 4.8 62,000 | 7.1 11,440,000 | 1.0 | 89.20 |

TABLE 1-continued

| | | Escherichia coli (N = 3) | | | |
|---|---|---|---|---|---|
| | | 0 hr | 18 hr | Antibacterial activity (growth value) | Reduction rate (%) |
| Autoclaved controls (standard textiles) | | 4.2 16,000 | 8.1 126,666,667 | 3.9 | 0 |
| Example 2 | 50 Times of washing | 3.9 8,000 | 1.3 20 | 6.8 | 99.99 |
| | 100 Times of washing | 3.8 6,000 | 1.3 20 | 6.8 | 99.99 |
| Comparative Example 1 | 50 Times of washing | 4.3 20,000 | 6.1 1,337,333 | 2.1 | 98.94 |
| | 100 Times of washing | 4.3 20,000 | 7.0 9,920,000 | 1.2 | 92.16 |

The results described in Table 1 provide the following. The textile sample of Example 2, after being washed 50 times and after being washed 100 times, exhibited good antibacterial activity against all of *Staphylococcus aureus*, *Klebsiella pneumoniae* and *Escherichia coli*. In contrast, the textile sample of Comparative Example 1 decreased its antibacterial activity and showed a lower bacterial reduction rate against all of *Staphylococcus aureus*, *Klebsiella pneumoniae* and *Escherichia coli* after 100 times of washing as compared to after 50 times of washing.

The textile samples of Example 2 and Comparative Example 1 differ in that the base material in the textile sample of Example 2 is titanium dioxide marketed as a white pigment while the base material is alumina in the textile sample of Comparative Example 1. Alumina is a component that is known to have no photocatalytic activity. Thus, the titanium dioxide sold as a white pigment that was used in the textile sample of Example 2 probably had slight photocatalytic activity and gave rise to differences in antibacterial activity and bacterial reduction rate between the textile sample of Example 2 and the textile sample of Comparative Example 2.

Based on the above assumption, the results of Example 2 and Comparative Example 1 will show the following facts. Titanium dioxide used as the base material has low but a certain level of photocatalytic activity. By virtue of this slight photocatalytic activity in combination with the configuration corresponding to the agent of Example 1 or Example 2, textile samples treated with the agent can exhibit high antibacterial activity and can remain highly active against bacteria even after being washed a large number of times.

While Example 1 and Example 2 have illustrated the adsorption of silver ions to the titanium dioxide base material and the hydroxyapatite, the ions that are adsorbed are not limited to silver ions but may be gold ions ($Au^{3+}$, platinum ions ($Pt^{2+}$) or copper ions ($Cu^{2+}$). Furthermore, Example 1 and Example 2 have illustrated that silver ions are formed by electrolysis, but silver ions, or gold ions, platinum ions or copper ions may be supplied by the addition of an aqueous solution of, for example, silver nitrate ($AgNO_3$), gold chloride ($AuCl_3$), platinum chloride ($PtCl_2$), cupric chloride ($CuCl_2$) or cupric nitrate ($Cu(NO_3)_2$).

Furthermore, while Example 1 and Example 2 have involved hydroxyapatite in addition to the titanium dioxide base material, hydroxyapatite is not necessarily essential and may be eliminated. However, the use of hydroxyapatite, which is known to adsorb various components, offers enhancements not only in antibacterial activity but also in bacterial reduction rate.

Furthermore, in Example 1 and Example 2, silver ions were adsorbed to titanium dioxide and hydroxyapatite by allowing the system to stand still overnight. However, manual stirring, mechanical stirring, ultrasonication, inert gas bubbling or ball mill stirring may be adopted to accomplish the adsorption quickly.

In Example 1 and Example 2, titanium dioxide known as a pigment was used as the base material. Any commercial titanium dioxide having lower photocatalytic activity than photocatalytically active titanium dioxide may be appropriately selected for use in the present invention. Such titanium dioxide does not necessarily need to be of high purity, and may be purchased at a low price. The binder used in Example 1 and Example 2 is an acrylic resin, but other binders such as glyoxal resins and butadiene resin latexes may also be used.

Antibacterial Activity Evaluation 2

In Antibacterial Activity Evaluation 2, the persistence of antibacterial activity was evaluated in the same manner as in Antibacterial Activity Evaluation 1, except that the number of washing was increased to 200 times and further to 300 times. The textile sample that was used was similar to that obtained in Example 2. The evaluation procedures were the same as in Antibacterial Activity Evaluation 1.

To avoid confusion with the results of Antibacterial Activity Evaluation 1, the results obtained here will be written as the evaluation results 2.

Two types of bacteria were used:
(i) *Staphylococcus aureus*, and
(ii) *Escherichia coli*. Three sheets of the textile sample of Example 2 were repeatedly washed 100 times (100 times of washing), and other triplets of the textile sample were repeatedly washed 200 times (200 times of washing) or 300 times (300 times of washing). With respect to these washed sheets, the antibacterial activity was evaluated by measuring the bacterial counts immediately after the inoculation and after 18 hours, the results being averaged. The evaluation results 2 are described in Table 2.

The values in the "Immediately after inoculation" column and the "After 18 hours" column in Table 2 are the common logarithms of the bacterial counts obtained. The antibacterial activities (the growth values) are values determined from the following equation:

$$\text{Antibacterial activity (growth value)} = (\log B - \log A) - (\log D - \log C)$$

A: Viable bacterial count on standard textile immediately after inoculation
B: Viable bacterial count on standard textile after incubation C: Viable bacterial count on sample immediately after inoculation
D: Viable bacterial count on sample after incubation

TABLE 2

| | Staphylococcus aureus | | | Escherichia coli | | |
| | Common logarithms of bacterial counts | | | Common logarithms of bacterial counts | | |
| Samples | Immediately after inoculation | After 18 hours | Antibacterial activity | Immediately after inoculation | After 18 hours | Antibacterial activity |
| --- | --- | --- | --- | --- | --- | --- |
| No washing | 4.53 | 1.30 | 5.7 | 4.41 | 1.30 | 6.4 |
| 100 Times of washing | 4.40 | 1.30 | 5.7 | 4.35 | 1.30 | 6.4 |
| 200 Times of washing | 4.46 | 1.30 | 5.7 | 4.35 | 1.30 | 6.4 |
| 300 Times of washing | 4.49 | 1.30 | 5.7 | 4.32 | 1.30 | 6.4 |
| Controls | 4.54 | 7.03 | | 4.5 | 7.72 | |

The results described in Table 2 provide the following. The evaluation results 2 have shown that the textile sample of Example 2, after being washed 200 times and after being washed 300 times, exhibited good antibacterial activity against Staphylococcus aureus and Escherichia coli. Furthermore, the evaluation results 2 indicated that the textile sample would have shown good antibacterial activity even after more than 300 times of washing, and would have satisfied longer persistence in line with the advantageous effects of the present invention.

The agents according to the present invention are excellent in persistence as shown by the results in Table 2. However, the binder serving as an adhesive or a fixer may leach out gradually due to external stress that is expected during repeated washing in the future. Thus, safer binders will be required.

To be safe, the binder used for bonding and fixation will be one that uses a thermosetting polycarbodiimide curing agent and is free from preservatives. By rendering the binder used in the agent thermosetting, the agent according to the present invention attains higher safety and becomes environmentally friendly and persistent.

The agents according to the present invention may be used on target objects such as wood, cloth, plastics, metals, ceramics, concretes, etc. by being bonded thereto, for example, by being coated thereto; they may also be used as inside filler materials as well. While the agents according to the present invention are useful as described above, the agents may constitute useful materials by being dispersed in dispersing agents such as water, organic solvents, adhesives, etc.

In addition to the above forms, the agents according to the present invention may take the forms of printing inks and paint materials. These forms aim to provide sterilization and deodorizing effects, and also decorative effects. Printing inks and other forms of the present invention are not limited to containing the ceramic to which a metal is bonded, and hydroxyapatite as an adsorptive material, and may contain at least color materials and carriers. Printing inks may contain other ingredients as required. As the color materials, the following can be listed: inorganic colorants (pigments), organic colorants (pigments) (i.e., color materials commonly used for printing inks), and dyes such as solvent dyes (dyes dissolved in organic solvents), disperse dyes, etc. Some examples of the carriers are described below.

As the carriers, the following can be listed: oils, for example, drying oils such as linseed oil, etc., semidrying oils such as soybean oil, etc., and nondrying oils such as castor oil, etc.; resins, for example, natural resins (such as pine resin (rosin), modified pine resin (modified rosin), gilsonite, etc.), natural resin derivatives, phenol resins, alkyd resins, xylene resins, urea resins, melamine resins, polyamide resins, acrylic resins, epoxy resins, ketone resins, petroleum resins, polyvinyl chloride resins, polyvinyl acetates, urethane resins, chlorinated polypropylenes, chlorinated rubbers, cyclized rubbers, cellulosic derivatives and reactive resins; and plasticizers.

Other materials are also usable, with examples including wax components in natural waxes and synthetic waxes, dryers, dispersing agents, wetting agents, cross-linking agents, gelling agents, thickening agents, anti-skinning agents, stabilizers, flattening agents, anti-foaming agents, anti-flooding agents, anti-fungus agents, etc.

There is no critical limit on the mixing ratio for these components, and the components may be used in a mixing ratio generally found in commercial printing inks. In order to ensure that the printing ink will have sterilizing effects, will exert the effects of, for example, eliminating odors, and will show appropriate printability, the agent according to the present invention is preferably added to represent 3 to 80%, more preferably 10 to 80%, of the total weight of the printing ink.

The forms or kinds of the printing inks are not particularly limited. The printing inks may be paste inks, solvent inks, or solvent-free inks. The inks may also be used as offset printing inks, lithographic printing inks, photogravure printing inks, screen process printing inks, letterpress printing inks, or special printing inks. In order to best achieve the purpose of the present invention, screen process printing inks, for example, screen process printing inks for paper, screen process printing inks for plastics, screen process printing inks for glass, screen process printing inks for metals, screen process printing inks for cloth, etc., are preferred among the aforementioned types.

In addition to the above, the agents according to the present invention may be used in other forms explained below. Paint materials contain not only the agent according to the present invention, but also at least film forming components and dispersing agents. Additional components may be contained if necessary. As the film forming components, the following can be listed: synthetic resins such as cellulosic derivatives, phthalate resins, phenol resins, alkyd resins, amino alkyd resins, acrylic resins, epoxy resins, urethane resins, polyvinyl chloride resins, silicone resins, fluororesins, emulsions, water-soluble resins, etc.; and vegetable drying oils.

As the dispersing agents, the following can be listed: petroleum solvents, aromatic solvents, alcohol solvents, ester solvents, ketone solvents, cellosolve solvents, water, etc. In the case of powder paints, solvents as dispersing agents are not necessary.

As the additional components, the following can be listed: colorants (pigments), for example, inorganic (colorants) pigments such as titanium dioxide, lead chromate, red oxide (Indian red), chrome oxide, carbon black, etc., organic colorants (pigments) such as Hansa yellow, Novoperm orange, quinacridone violet, copper phthalocyanine, etc.; body pigments such as precipitated calcium carbonate, barium sulfate, talc, clay, white carbon, etc.; and special functional colorants (pigments) represented by anti-corrosive pigments such as zinc chromate, strontium chromate, zinc phosphate, aluminum phosphate, etc.

Furthermore, for example, the following may be incorporated as supplementary materials: dryers (drying agents) and polymerization catalysts for accelerating the drying of paint films; wetting agents, pigment dispersion agents, anti-flooding agents, anti-setting agents for improving the dispersibility of colorants (pigments), thickening agents, thixotropic agents, anti-sagging agents for regulating the fluidity of colorants (pigments); and leveling agents, anti-foaming agents, anti-crawling agents, anti-floating agents as well as plasticizers, anti-skinning agents, electrostatic coating adjuvants, anti-scratch agents, anti-blocking agents, anti-UV agents, antifouling agents, antiseptic agents, anti-fungus agents, etc. for regulating the painted surface. The ratio in which these components are added is not particularly limited and may be determined appropriately in light of the technical knowledge of one of ordinary skill in the art.

In this case, a compounding ratio generally found in commercial painting materials may be used. In order to ensure that the paint material will have sterilizing effects, will exert the effects of, for example, eliminating odors, and will show appropriate paintability, the content of the agent according to the present invention is preferably 3 to 80%, and more preferably 10 to 80% of the total weight of the paint material.

The coating methods for the paint materials are not particularly limited. Methods may be used such as paintbrush coating, air spray coating, airless spray coating, electrostatic spray coating, powder coating, electro-deposition coating, curtain flow coating, roller-brush coating, etc. The area to be coated with the agent according to the present invention is not particularly limited and is variable depending on how the agent is used.

The agents according to the present invention may be used by being mixed with liquid solutions or agents that can be applied to the human body or other surfaces represented by such forms as ointments, skin lotions, etc., and thereby impart effects such as sterilizing effects, deodorizing effects, etc. For example, the agents may be mixed with liquid solutions or agents to give a variety of products such as cosmetics, hand creams 11 illustrated in FIG. 3, ointments, ointments for medical treatment (for troubles that are associated with skin and epidermis such as tinea pedis, burn (scald), bedsore (decubitus), secondary diseases of atopic dermatitis, wounds, etc.).

Other than with liquid solutions or agents, the agents according to the present invention may be mixed with products such as resins, ceramics, adhesives, etc., and also may be mixed with raw materials for making materials.

The agents according to the present invention may be attached to various materials such as paper, wood, cloth, plastics, metals, concretes, etc. to offer effects such as sterilizing effects, deodorizing effects, etc. Furthermore, the agents according to the present invention may exert decorative effects by being printed into desired patterns or graphics, and may be used for a variety of decorations and other purposes that will not use light irradiation. For example, the agents according to the present invention may be attached to ceramics, metals and compound materials to serve in a variety of products such as purification (FIG. 4A) of drinking water 12 illustrated in FIG. 3, preservation of drinking water 12, storage of rainwater (FIG. 4B), re-use of rainwater, reservoirs, ponds, washing and cleaning of vegetables, hydroponic culture (including aquaculture), cooling towers illustrated in FIG. 4C, bathtubs, hot spring, soil amendment illustrated in FIG. 4D, foodstuff preservation, freshness-keeping of foodstuffs, drain outlets and ditches, tiles 13 illustrated in FIG. 3, humidifiers 14 illustrated in FIG. 3, medical equipment, column fillers, etc.

Figure 3:
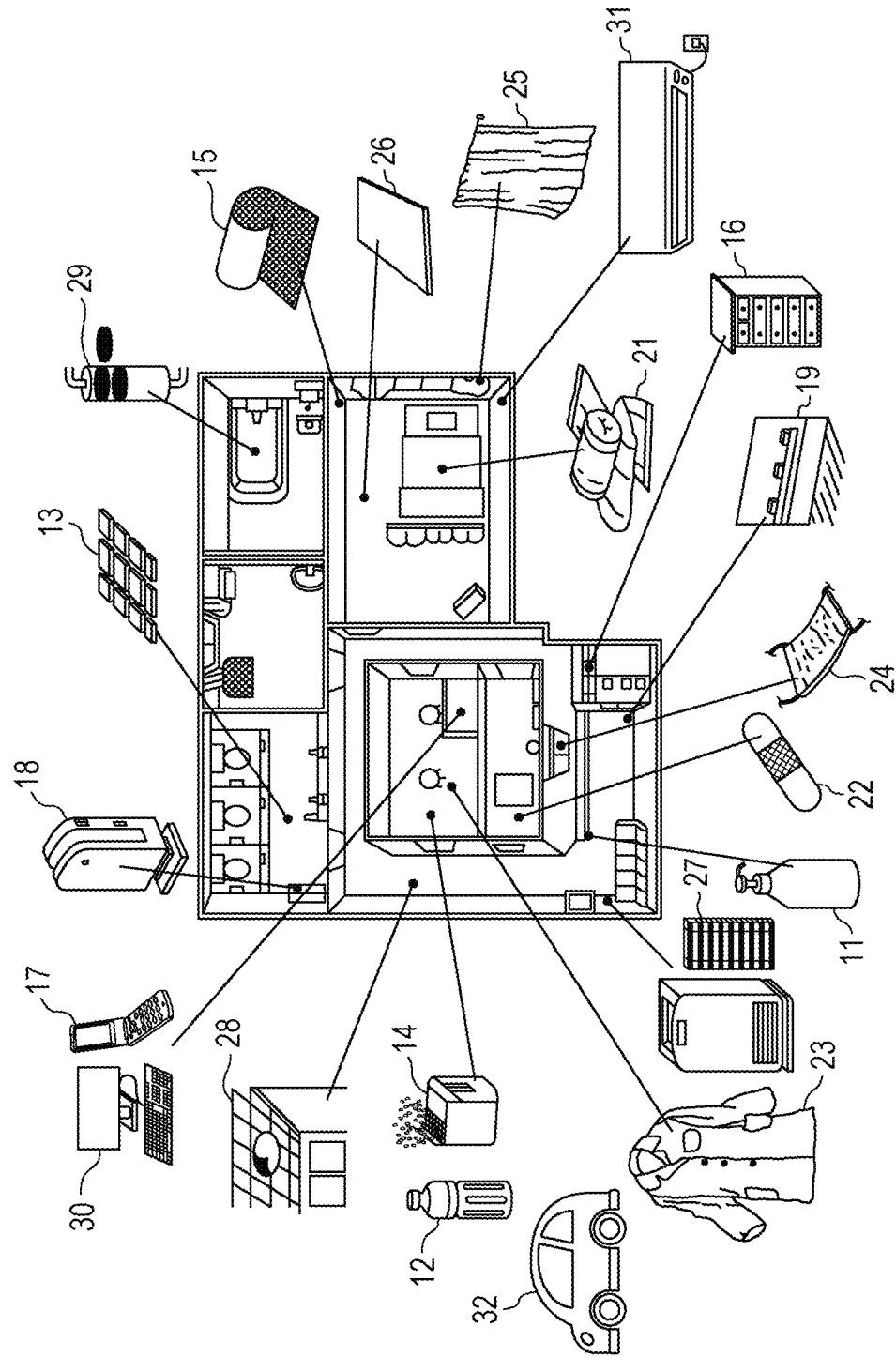
FIG. 3 is a view illustrating use of agents according to the present invention for a variety of products.
Figure 4A:
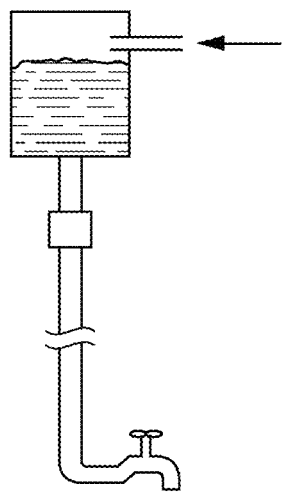
FIG. 4A is a view of an agent according to the present invention used for drinking water.
Figure 4B:
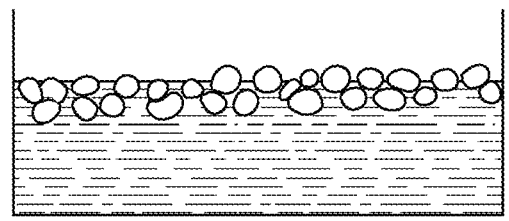
FIG. 4B is a view of an agent according to the present invention used for preservation of drinking water.
Figure 4C:
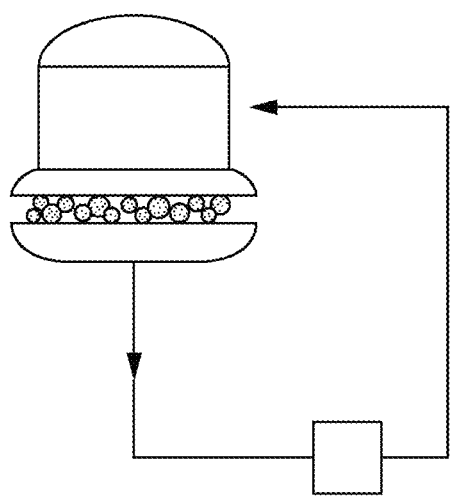
FIG. 4C is a view of an agent according to the present invention used for preservation in a cooling tower.
Figure 4D:
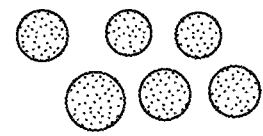
FIG. 4D is a view of an agent according to the present invention used for soil amendment.

Furthermore, the agents according to the present invention may be attached to paper to usefully serve as housing materials, such as various wrapping papers, bags, etc. for materials and products, including foodstuff preservation, filters, medical materials, medical products, wallpapers 15 illustrated in FIG. 3, shoji papers, fusuma papers, outer surface materials of furniture 16 illustrated in FIG. 3, etc. In addition, the agents according to the present invention may be attached to resins to usefully serve as, for example, various kinds of films such as decorative films, protective films and foodstuff wrapping films, resin products in the medical field such as catheters, endoscopes, balloons and instrument buttons, products such as personal computers 30 illustrated in FIG. 3, telephones 17 illustrated in FIG. 3, jet-towels 18 illustrated in FIG. 3 and play equipment, and housing materials such as handrails 19 illustrated in FIG. 3 and ceiling materials 28 illustrated in FIG. 3. Furthermore, the agents according to the present invention are useful as materials needed for manufacturing these products described above. The agents are also useful as sizing agents that are contained in raw materials for paper, woven fabrics or nonwoven fabrics.

The agents according to the present invention may be attached to cloth (textile materials) and woven fabrics to usefully serve as various products such as cloths 21 illustrated in FIG. 3, materials for foodstuffs illustrated in FIG. 3, materials for agriculture use, materials for medical use, adhesive plasters (adhesive bandages) 22 illustrated in FIG. 3, gauzes, bandages, gowns 23 illustrated in FIG. 3, uniforms, face masks 24 illustrated in FIG. 3, curtains 25 illustrated in FIG. 3, bedclothes (sheets), futon covers, blanket covers, pillow cases, etc., various covers (seat covers, floor cushion covers, etc.), table clothes, carpets 26 illustrated in FIG. 3, towels, handkerchiefs, etc. Furthermore, the agents according to the present invention may be used as materials for air-purification filters 27 illustrated in FIG. 3, or water-purification filters 29 illustrated in FIG. 3.

Furthermore, the agents according to the present invention may be used in air conditioners 31 and vehicles 32 illustrated in FIG. 3. For example, the agents may be used in filters of the air conditioners 31, and in air conditioners, seats, seat covers, interiors, etc. of the vehicles 32. Furthermore, the agents according to the present invention may be used for the painting of buildings and other structures, for the painting of various products, and as additives in antifouling paints for ships, bridges, piers (bridge supports), etc. for purposes such as to repel (protect from the attachment of)

aquatic organisms such as acorn barnacles, Serpula, Mytilus, etc. The agents may also be used to prevent the generation of algae.

The agents according to the present invention adsorb bacteria, viruses and fungi, as well as odor substances, harmful substances, toxic substances, etc. Following their adsorption or at the same time as their adsorption, the bacteria, viruses, fungi, etc. are decomposed. Furthermore, the agents according to the present invention can effectively stop the growth of, or repel, whatever is not decomposed. Furthermore, without light irradiation the agents according to the present invention have the same effects as they have under light irradiation at ambient temperatures for human beings living on the Earth. Moreover, proteins constituting bacteria, viruses, fungi, etc. are decomposed and disappear, and therefore the aforementioned effects do not diminish with time and do last semi-permanently.

Bacteria, fungi, etc. favor high temperatures and high humidities to multiply. The agents according to the present invention are effective particularly under high-temperature and high-humidity conditions and are therefore effective also for the destruction of bacteria and fungi. The sterilizer components in the agents according to the present invention are insoluble, and therefore the agents according to the present invention may be used in a very wide range of applications that kill and suppress the growth of undesirable microorganisms such as bacteria, fungi, etc. In places such as houses, hospitals, nursing homes, public facilities, food factories, water plants, etc., a difficulty in handling public hygiene, bacteria control, odor control, etc., with one product may be overcome by using the agents according to the present invention together with other products appropriately combined to meet the demands. Such a "system" is extremely effective in sterilizing bacteria and eliminating odors. In order to attain further effects in a wider range of fields, the agents according to the present invention may be used in combination with existing medicaments, and various products or systems that are generally used, so as to constitute a novel sterilizing system (a novel sterilizing method) that has instantaneous and continuous effects. For example, target objects may be sterilized with alcohols first, and may be thereafter kept sterilized with the agents according to the present invention for long periods of time.

Furthermore, the agents according to the present invention are substantially insoluble and do not burden the environment. There are a variety of conventional medical products for sterilizing bacteria, deactivating viruses, decomposing allergens, and eliminating odors. However, the fact is that such medical products are more intrinsically destructive to the human body and the nature with increasing efficacy. In contrast, the agents according to the present invention are insoluble in water and remain effective for long periods of time, and are thus safe and do not adversely affect the environment. Furthermore, the agents according to the present invention are as effective without light irradiation continuously for long periods of time as they are under light irradiation, and exhibit similar effects also under natural light. Therefore, the agents according to the present invention are useful in a wide range of applications, making great contributions to the industry.

As discussed hereinabove, the agents according to the present invention have efficacy against at least one of viruses, allergens, bacteria, fungi, odorants, harmful substances and the like, and can decompose dead organisms such as of viruses, bacteria and fungi, allergens, odor substances and further soiling substances by contact with the metal ions and metal oxide, over long periods of time irrespective of whether light is present.

Furthermore, the agents according to the present invention are useful in anti-infection measures in medical-related facilities susceptible to bacterial and viral propagation through contact.

Furthermore, the agents according to the present invention are less expensive than the conventional agents, compare equally at a small dose to the conventional agents in the aforementioned effects, and are environmentally friendly and safe.

What is claimed is:

1. An agent having efficacy against at least one of viruses, allergens, bacteria, fungi and odorants, the agent comprising:
   titanium dioxide particles having low photocatalytic activity, and
   metal ions of at least one metal selected from gold, silver, platinum or copper that are adsorbed to the surface of the titanium dioxide particles,
   wherein the metal ions are present in the form of at least one of metal oxide or metal hydroxide.

2. The agent according to claim 1, further comprising hydroxyapatite particles, the metal ions being adsorbed also to the surface of the hydroxyapatite.

3. The agent according to claim 1, wherein the agent is efficacious against at least one of viruses, allergens, bacteria, fungi and odorants by way of contact.

4. A material comprising the agent of claim 1.

5. The material according to claim 4, applied to at least one substrate selected from:
   (a) at least one of fibers of any of woven fabrics, nonwoven fabrics and paper, wood, plastics, metals and ceramics;
   (b) compound materials formed of two or more of woven fabrics, nonwoven fabrics, paper, wood, plastics, metals and ceramics; and
   (c) at least one of paints, resin films, water, cleaning solutions, air filters and printing inks.

6. The material according to claim 5, wherein
   the substrate is fibers of any of a woven fabric, a nonwoven fabric and paper; and
   the fibers are impregnated with the agent by immersion of the fibers into a solution in which the agent is dispersed in a solvent.

7. The material according to claim 5, wherein
   the substrate is fibers of any of a woven fabric, a nonwoven fabric and paper; and
   the agent is attached to the surface of the fibers by application, to the surface of the fibers, of a solution in which the agent is dispersed in a solvent.

8. The material according to claim 5, wherein
   the substrate is at least one of wallpapers, ceiling materials, flooring materials and furniture; and
   a solution in which the agent is dispersed in a solvent is applied to the surface of the substrate, or a resin film including the agent is applied to the surface of the substrate.

9. The material according to claim 4, applied to any of drinking water, rainwater, hot spring and cooling towers.

10. The material according to claim 4, applied to any of hydroponic culture, aquaculture, soil amendment, washing of vegetables, cleaning of vegetables, foodstuff preservation and foodstuff antisepsis.

11. The agent according to claim 4, wherein the material is fibers and the agent is attached to a surface of the fibers.

12. A product comprising the agent of claim 1.

13. The product according to claim 12, wherein the product is a product selected from fibrous sheets, bed sheets, pillow cases, towels, handkerchiefs, bed-bath cloths, curtains, futon covers, blanket covers, seat covers, floor cushion covers, covers, table clothes, carpets, airpurification filters, water-purification filters, air conditioners and vehicles.

14. The product according to claim 12, wherein the product is a medical item selected from medical materials, medical elements, medical products and medical equipment.

15. The product according to claim 12, wherein the product is a product selected from adhesive plasters, adhesive bandages, ointments, skin lotions, cosmetics, hand creams, gauzes, catheters, endoscopes, bandages, gowns, face masks, balloons, medical instrument buttons, and resin products for medical use.

16. The product according to claim 12, wherein the product is a product selected from medical agents applied to at least one of tinea pedis, burn, scald, bedsore, decubitus, secondary diseases of atopic dermatitis, wounds in the skin, and wounds in the epidermis.

17. The product according to claim 12, wherein the product is a product for infection control.

18. A method for producing an agent having efficacy against at least one of viruses, allergens, bacteria, fungi and odorants of claim 1, the method comprising:
   a first step of providing a solution including metal ions of at least one metal selected from gold, silver, platinum or copper,
   a second step of immersing titanium dioxide particles having low photocatalytic activity into the solution and thereby adsorbing the metal ions to the surface of the titanium dioxide particles, and
   a third step of drying the particles obtained at the second step;
   wherein the metal ions are present in the form of at least one of metal oxide or metal hydroxide.

19. The method for producing an agent according to claim 18, wherein hydroxyapatite particles are present at the second step.

20. The method for producing an agent according to claim 18, wherein the metal ions of at least one metal provided at the first step are formed by electrolysis of the at least one metal, or by addition of a salt of the at least one metal.

21. The method for producing an agent according to claim 18, wherein the second step is performed by manual stirring, mechanical stirring, ultrasonication, inert gas bubbling or ball mill stirring.

22. The method for producing an agent of claim 18, and an agent produced thereby, wherein the third step comprises, concurrently with the drying of the particles obtained at the second step, bonding or fixing the particles.

23. The method for producing an agent of claim 22, and an agent produced thereby, wherein the particles are bonded or fixed at the third step using a thermosetting polycarbodiimide curing agent as a binder.

* * * * *